(12) United States Patent
Niimi et al.

(10) Patent No.: US 9,239,309 B2
(45) Date of Patent: Jan. 19, 2016

(54) HUMIDITY SENSOR AND METHOD OF MANUFACTURING THE SAME

(75) Inventors: Naohisa Niimi, Kariya (JP); Minekazu Sakai, Kariya (JP)

(73) Assignee: DENSO CORPORATION, Kariya (JP)

( * ) Notice: Subject to any disclaimer, the term of this patent is extended or adjusted under 35 U.S.C. 154(b) by 211 days.

(21) Appl. No.: 14/115,901

(22) PCT Filed: May 30, 2012

(86) PCT No.: PCT/JP2012/003530
§ 371 (c)(1),
(2), (4) Date: Nov. 6, 2013

(87) PCT Pub. No.: WO2012/169148
PCT Pub. Date: Dec. 13, 2012

(65) Prior Publication Data
US 2014/0077824 A1    Mar. 20, 2014

(30) Foreign Application Priority Data
Jun. 6, 2011   (JP) ................... 2011-126375

(51) Int. Cl.
*G01N 27/22* (2006.01)
*G01N 27/12* (2006.01)

(52) U.S. Cl.
CPC ............ *G01N 27/223* (2013.01); *G01N 27/121* (2013.01)

(58) Field of Classification Search
CPC .. G01N 27/223; G01N 27/121; G01N 27/225
USPC .................................................. 324/661–664
See application file for complete search history.

(56) References Cited

U.S. PATENT DOCUMENTS

2006/0037404 A1    2/2006  Watanabe
2006/0238290 A1*  10/2006  Arisaka ........................ 338/35
2009/0056439 A1*   3/2009  Suzuki ...................... 73/335.02

FOREIGN PATENT DOCUMENTS

| JP | 2002-071612 A | 3/2002 |
| JP | 2005-291886 A | 10/2005 |
| JP | 2006-060015 A | 3/2006 |
| JP | 2006-337110 A | 12/2006 |
| JP | 2008-064561 A | 3/2008 |
| JP | 2010-237095 A | 10/2010 |

OTHER PUBLICATIONS

Office Action dated Feb. 15, 2015 issued in corresponding CN patent application No. 201280027927.3 (and English translation).
International Search Report and Written Opinion of the International Searching Authority mailed Aug. 28, 2012 for the corresponding international application No. PCT/JP2012/003530 (with English translation).

* cited by examiner

*Primary Examiner* — Vincent Q Nguyen
(74) *Attorney, Agent, or Firm* — Posz Law Group, PLC (57) ABSTRACT

A humidity sensor includes a humidity detention section, a pad section, and a dam section. The humidity detention section includes a pair of detection electrodes facing each other on a predetermined surface of a substrate and a humidity-sensitive film covering the detection electrodes. The pad section is spaced from the humidity detection section on the surface and covered with a protection gel section. The dam section is located between the humidity detection section and the pad section on the surface. The dam section includes a dam wire that is made from the same material as the detection electrodes and a dam humidity-sensitive film that is made from the same material as the humidity-sensitive film and covers at least part of the dam wire.

16 Claims, 5 Drawing Sheets

HUMIDITY SENSOR AND METHOD OF MANUFACTURING THE SAME

CROSS REFERENCE TO RELATED APPLICATION

This application is a U.S. national stage application of PCT/JP2012/003530 filed on May 30, 2012, and is based on Japanese Patent Application No. 2011-126375 filed on Jun. 6, 2011, the contents of which are incorporated herein by reference.

TECHNICAL FIELD

The present disclosure relates to a humidity sensor and a method of manufacturing the humidity sensor including a pair of detection electrodes arranged to face each other and a humidity-sensitive film that covers the detection electrodes and a gap between the detection electrodes.

BACKGROUND ART

As disclosed in, for example, patent documents 1 and 2, humidity sensors are known.

In the patent document 1, a pair of comb-shaped electrodes is formed on a surface of a substrate, and a frame member made from a foam material is arranged around the comb-shaped electrodes. The whole area inside the frame member is covered with a humidity-sensitive film. Further, a pad section as an external connection terminal is formed on the substrate outside the frame member.

In the patent document 2, a humidity detection section and a circuit section are formed on the same substrate. The humidity detection section includes a pair of detection electrodes and a humidity-sensitive film. The circuit section processes an output signal from the humidity detection section. The pair of detection electrodes face each other on the same surface of the substrate are spaced from each other. The humidity-sensitive film covers the detection electrodes and a gap between the detection electrodes. Further, a pad (not shown) of the circuit section is connected to a bonding wire, and a dam section is formed between the humidity detection section and the pad section (the circuit section) of the substrate.

By the way, the pad section is generally made from aluminum based on the cost front, for example. Therefore, there is a concern that the pad section will be corroded when the humidity sensor is used in humidified atmosphere. In the patent document 2, a protection gel section made from a water-resistant material covers the pad section and protects the pad section from corrosion.

However, the protection gel section has flowability yet when the protection gel section is applied. Then, a hardening process is performed so that the protection gel section can be fixed in a predetermined position. Therefore, when the protection gel section having the flowability is applied to the pad section, the protection gel section may flow and adhere to a surface of the humidity-sensitive film. In such a case, a property of the humidity-sensitive film may be changed so that humidity detection accuracy may be reduced.

In the patent document 1, adhesion of the protection gel section to the humidity-sensitive film is reduced by the dam section. In the patent document 2, the adhesion of the protection gel section to the humidity-sensitive film is reduced by the frame member.

PRIOR ART

Patent Document

Patent Document 1: JP-A-2008-64561
Patent Document 2: JP-A-2002-71612

By the way, in the patent document 2, the dam section is formed by applying polyimide, as a material for the humidity-sensitive film, to a region where the humidity detection section is formed while applying polyimide to a region where the dam section is formed. Since the humidity-sensitive film and the dam section are formed at the same time, a structure of the humidity sensor is simplified. Also, a manufacturing process is simplified.

However, in the patent document 2, like the humidity-sensitive film, the dam section is made from only polyimide. Since the height of the dam section depends on formation conditions of the humidity-sensitive film, it is difficult that the dam section is made extremely higher (thicker) than the humidity-sensitive film. Therefore, if the amount of the protection gel section to be applied is large, the protection gel section may flow to the humidity detection section across the dam section and adhere to the humidity-sensitive film.

In the patent document 2, the frame member is formed as a separate piece from the humidity-sensitive film. Therefore, the height of the frame member can be set to a desired height regardless of the formation conditions of the humidity-sensitive film. However, since the frame member is formed as a separate piece from the other members of the humidity sensor, the number of parts of the humidity sensor is increased. Accordingly, the manufacturing process becomes complicated. The increase in the number of parts and the complication of the manufacturing process will be largely reflected in an increase in a manufacturing cost. As a result, the humidity sensor will be costly.

SUMMARY OF THE INVENTION

In view of the above, it is an object of the present disclosure to provide a humidity sensor and a method of manufacturing the humidity sensor to effectively reduce adhesion of a protection gel section to a humidity-sensitive film while simplifying a structure and a manufacturing process.

According to a first aspect of the present disclosure, a humidity sensor includes a humidity detention section, a pad section as an external connection terminal, and a dam section. The humidity detention section includes a pair of detection electrodes facing each other on a surface of a substrate and a humidity-sensitive film covering the detection electrodes and a gap between the detection electrodes. The pad section is spaced from the humidity detection section on the surface of the substrate and covered with a protection gel section under a condition where a bonding wire is connected to the pad section. The dam section is located between the humidity detection section and the pad section on the surface of the substrate to restrain the protection gel section from flowing from the pad section side to the humidity detection section side.

The dam section includes a dam wire and a dam humidity-sensitive film. The dam wire is made from the same material as the detection electrodes and located on the same surface as the detection electrodes. The dam humidity-sensitive film is made from the same material as the humidity-sensitive film and covers at least part of the dam wire.

According to the first aspect, the dam wire of the dam section is formed on the same surface as the detection electrodes by using the same material as the detection electrodes.

Further, the dam humidity-sensitive film of the dam section is formed by using the same material as the humidity-sensitive film. Thus, a structure of the humidity sensor can be simplified in structure. Further, since the dam section is formed by using a process in which another portion of the humidity sensor is formed, a manufacturing process can be simplified.

Further, the dam section has a multilayer structure in which the dam humidity-sensitive film is located on the dam wire. Thus, the height of the dam section can be large as compared to when the dam section is constructed with only the dam humidity-sensitive film. Accordingly, the protection gel section becomes less likely to flow over the dam section, and adhesion of the protection gel section to a surface of the humidity-sensitive film can be effectively reduced.

Therefore, according to the first aspect, the structure and the manufacturing process can be simplified, and the adhesion of the protection gel section to the humidity-sensitive film can be effectively reduced.

According to a second aspect of the present disclosure, a method of manufacturing a humidity sensor includes an electrode formation step of forming a pair of detection electrodes on a predetermined surface of a substrate, a humidity detection section formation step of forming a humidity detection section by forming a humidity-sensitive film to cover the detection electrodes and a gap between the detection electrodes, and a pad section formation step of forming a pad section as a external connection terminal in such a manner that the pad section is spaced from the humidity detection section on the surface of the substrate and covered with a protection gel section under a condition where a bonding wire is connected to the pad section. The electrode formation step includes a dam wire formation step of forming a dam wire on the surface of the substrate between the humidity detection section and the pad section by using the same material as the detection electrodes. The humidity detection section formation step includes a dam section formation step of forming a dam section, which restrains the protection gel section from flowing from the pad section side to the humidity detection section side, by forming a dam humidity-sensitive film to cover at least part of the dam wire by using the same material as the humidity-sensitive film.

In the electrode formation step, the detection electrodes are formed, and the dam wire of the dam section is formed on the predetermined surface of the substrate by using the same material as the detection electrodes.

In the humidity detection section formation step, the humidity-sensitive film to cover the detection electrodes is formed, and the dam humidity-sensitive film of the dam section to cover at least part of the dam wire is formed by using the same material as the humidity-sensitive film.

Therefore, the same advantage as provided by the first aspect can be provided by the second aspect.

BRIEF DESCRIPTION OF THE DRAWINGS

The above and other objects, features and advantages of the present disclosure will become more apparent from the following detailed description made with reference to the accompanying drawings. In the drawings.

EMBODIMENTS OF THE INVENTION

Embodiments of the present disclosure are described below with reference to the drawings in which like reference numerals depict like elements. In plan views of FIG. 2, and FIGS. 7-10, a humidity-sensitive film, a dam humidity-sensitive film, and a connection humidity-sensitive film are hatched to indicate areas where they are formed.

First Embodiment

Figure 1:
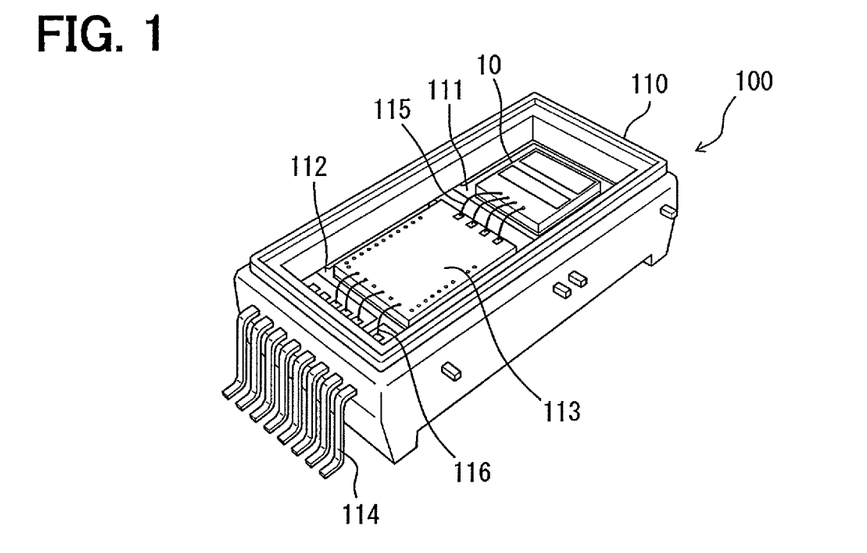
FIG. 1 is a diagram illustrating a perspective view of a humidity detection apparatus including a humidity sensor according to a first embodiment, in which a protection gel is omitted for the sake of convenience.

FIG. 1 shows a humidity detection apparatus 100 including a humidity sensor chip 10 according to a present embodiment. The humidity detection apparatus 100 includes a casing 110 made from synthetic resin and shaped like a rectangular tube with a bottom, lead frame islands 111 and 112 fixed to an inner surface of the bottom of the casing 110, a humidity sensor chip 10 mounted on the island 111, a circuit chip 113 mounted on the island 112, and a lead 114 having a first end located inside the casing 110 and a second end located outside the casing 110.

The humidity sensor chip 10 and the circuit chip 113 are electrically connected together by a bonding wire 115. The circuit chip 113 and the lead 114 are electrically connected together by a bonding wire 116. Although not shown in the drawings, the bonding wire 115, the bonding wire 116, and their connection portions (pads) are covered with a protection gel.

In this way, according to the present embodiment, the humidity sensor chip 10 is a separate chip from the circuit chip 113. The humidity sensor chip 10 corresponds to a humidity sensor recited in claims.

Next, a structure of the humidity sensor chip 10 is described.

Figure 2:
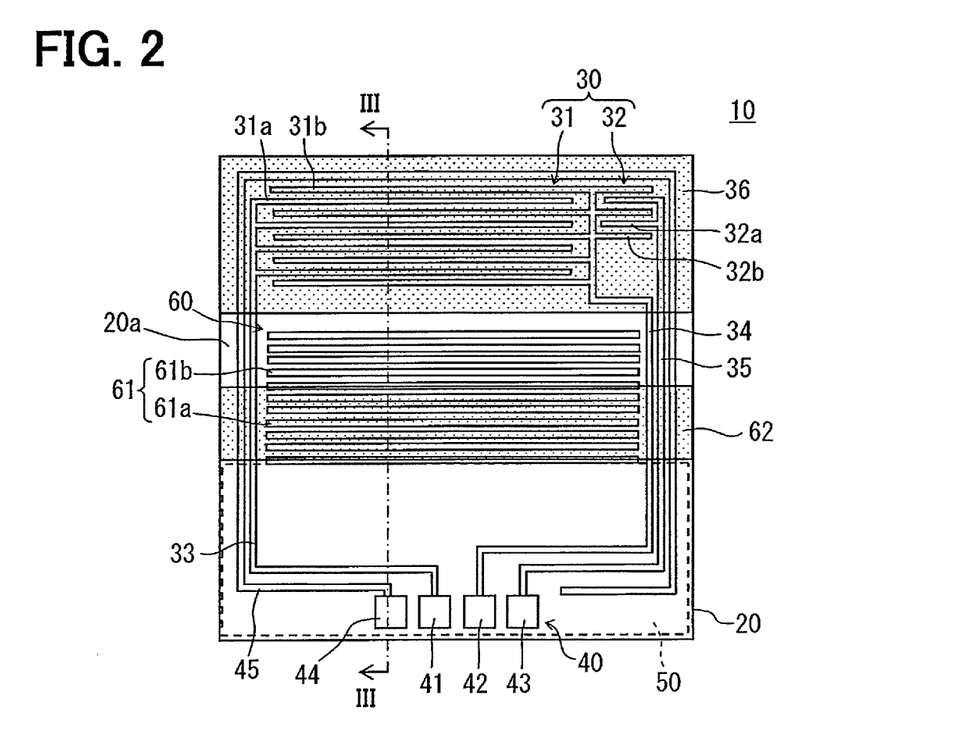
FIG. 2 is a diagram illustrating a plan view of the humidity sensor according to the first embodiment, in which a detection electrode, a reference electrode, a wire for connecting the electrodes to a pad, and a dummy wire are indicated by a solid line, and the protection gel is indicated by a broken line for the sake of convenience.
Figure 3:
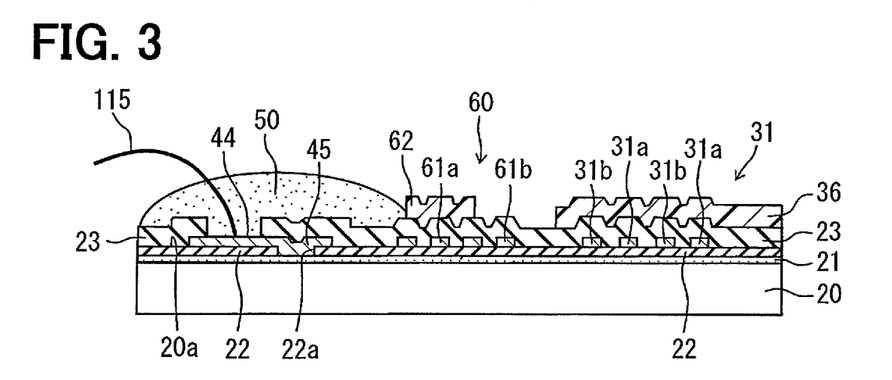
FIG. 3 is a diagram illustrating a cross-sectional view taken along the line III-III in FIG. 2, in which the wire for connecting the detection electrode to the pad is omitted, and the number of the detection electrodes and the dummy wires are reduced compared to FIG. 2.

As shown in FIGS. 2 and 3, in the humidity sensor chip 10, a humidity detection section 30, a pad 40 as an external connection terminal, and a dam section 60 for restraining a flow of a protection gel 50 are formed on a common substrate 20. The pad 40 is protected by the protection gel 50 under a condition where the bonding wire 115 is connected to the pad 40. The pad 40 corresponds to a pad section recited in claims, and the protection gel 50 corresponds to a protection gel section recited in claims.

According to the present embodiment, the substrate 20 is a silicon substrate, and an impurity diffusion layer 21 is formed in a surface portion of the whole of a first surface of the substrate 20. According to the present embodiment, the diffusion layer 21 is a p-conductivity type diffusion layer. An insulating layer 22 is located on the diffusion layer 21, and a contact hole 22a is formed in part of the insulating layer 22. According to the present embodiment, the insulating layer 22 includes a silicon oxide layer and a BPSG layer that are layered on top of each other in this order from the substrate 20 side. The humidity detection section 30, the pad 40, and the dam section 60 are formed on the insulating layer 22. Therefore, the substrate 20 and the insulating layer 22 are collectively referred to as a substrate, and an opposite side of the insulating layer 22 from the substrate 20 is referred to as a first surface 20a of the substrate 20. The first surface 20a corresponds to a humidity detection section formation surface recited in claims.

The humidity detection section 30 includes at least a detection capacitive device 31. According to the present embodiment, the humidity detection section 30 further includes a reference capacitive device 32. The detection capacitive device 31 has a pair of detection electrodes 31a, 31b that face each other on the first surface 20a of the substrate 20. The reference capacitive device 32 has a pair of reference electrodes 32a, 32b that face each other on the first surface 20a of the substrate 20 at a different position from where the detection electrodes 31a, 31b are located.

The shapes of the detection electrodes 31a, 31b and the reference electrodes 32a, 32b are not limited. According to the present embodiment, as shown in FIG. 2, the detection electrodes 31a, 31b have a comb-shape and are alternately arranged. Due to the comb-shape, while the layout area of the detection electrodes 31a, 31b is reduced, the overlapping area of the detection electrodes 31a, 31b is increased. Thus, a change in a capacitance between the detection electrodes 31a, 31b with respect to a change in ambient humidity is increased, so that the sensor sensitivity can be increased. Likewise, the reference electrodes 32a, 32b have a comb-shape and are alternately arranged Further, as shown in FIG. 2, the detection electrodes 31a, 31b differ from the reference electrodes 32a, 32b in the overlapping area and the number of teeth of the comb-shape. Specifically, the number of teeth of the detection electrodes 31a, 31b is larger than that of the reference electrodes 32a, 32b, and the overlapping area of the detection electrodes 31a, 31b is larger than that of the reference electrodes 32a, 32b.

The detection electrodes 31a, 31b and the reference electrodes 32a, 32b are made from the same material. Specifically, wiring material such as aluminum, copper, gold, platinum, or polysilicon is deposited by vapor deposition, sputtering, or the like. Then, in a photolithography process, a comb-shape is patterned. According to the present embodiment, the detection electrodes 31a, 31b, the reference electrodes 32a, 32b, and the pad 40 are made from aluminum. Therefore, as shown in FIG. 3, a protection layer 23 is formed on the detection electrodes 31a, 31b and the reference electrodes 32a, 32b, and a humidity-sensitive film 36 is formed on the protection layer 23.

The protection layer 23 protects the detection electrodes 31a, 31b and the reference electrodes 32a, 32b from corrosion due to water. According to the present embodiment, the protection layer 23 is a silicon nitride layer formed by a plasma CVD method. The protection layer 23 is formed on the first surface 20a of the substrate 20 to cover not only the detection electrodes 31a, 31b but also portions except the pad 40. When the detection electrodes 31a, 31b (and the reference electrodes 32a, 32b) have corrosion resistance to water, the protection layer 23 can be omitted.

The humidity-sensitive film 36 is formed on the protection layer 23 to cover the detection electrodes 31a, 31b, a portion between the detection electrodes 31a, 31b, the reference electrodes 32a, 32b, and a portion between the reference electrodes 32a, 32b. According to the present embodiment, the humidity-sensitive film 36 for covering the detection electrodes 31a and 31b and the humidity-sensitive film 36 for covering the reference electrodes 32a and 32b are integrated as a single humidity-sensitive film 36. The humidity-sensitive film 36 can be made from a known material such as a polyimide-type material. According to the present embodiment, the humidity-sensitive film 36 is made from a polyimide-type material. After precursor (polyamide) is coated by a spin coating method or a printing method, a heating and hardening treatment (an imidization treatment) is performed so that the humidity-sensitive film 36 can be formed.

In the humidity detection section 30, as shown in FIG. 2, the detection electrode 31a of the detection capacitive device 31 is electrically connected to a corresponding pad 41 through a wire 33. The detection electrode 31b of the detection capacitive device 31 and the reference electrode 32b of the reference capacitive device 32 are electrically connected to a corresponding pad 42 through a common wire 34. The reference electrode 32a of the reference capacitive device 32 is electrically connected to a corresponding pad 43 through a wire 35. Thus, a capacitor constructed with the pair of the detection electrodes 31a, 31b is connected in series with a capacitor constructed with the pair of the reference electrodes 32a, 32b between the pads 41 and 43, and a connection point (midpoint) between these capacitors is connected to the pad 42.

These wires 33-35 are formed on the first surface 20a of the substrate 20, i.e., on the same plane as the detection electrodes 31a, 31b and the reference electrodes 32a, 32b. Further, like the detection electrodes 31a, 31b and the reference electrodes 32a, 32b, the wires 33-35 are made from aluminum and covered with the protection layer 23.

The pads 41-43, which are electrically connected to the electrodes 31a, 31b, 32a, and 32b of the humidity detection section 30, are included in the pad 40. End portions of the wires 33-35 on the far side from the humidity detection section 30 are exposed through the opening of the protection layer 23 and serve as the respective pads 41-43. That is, the pads 41-43 are made from the same aluminum as the detection electrodes 31a, 31b and the reference electrodes 32a, 32b.

According to the present embodiment, the pad 40 further includes a pad 44 which is electrically connected to the diffusion layer 21. A wire 45 extending along an edge of the substrate 20 having a rectangular planar shape is connected to the pad 44. As shown in FIG. 3, a portion of the wire 45 is exposed through the opening of the protection layer 23 and serves as the pad 44. The wire 45 is also formed on the first surface 20a of the substrate 20, i.e., on the same plane as the detection electrodes 31a, 31b and the reference electrodes 32a, 32b. Further, like the detection electrodes 31a, 31b and the reference electrodes 32a, 32b, the wire 45 is made from aluminum and covered with the protection layer 23. As shown in FIG. 3, the contact hole 22a of the insulating layer 22 is filled with the wire 45 so that the wire 45 can be electrically connected to the diffusion layer 21. Therefore, when a constant potential (e.g., ground potential) is applied to the wire 45 through the pad 44, the diffusion layer 21 can function as a shield layer against electromagnetic waves.

The pad 40 (41-44) is covered with the protection gel 50 under the condition where the bonding wire 115 is connected to the pad 40. That is, before the bonding wire 115 is connected to the pad 40, the humidity sensor chip 10 does not have the protection gel 50. The protection gel 50 protects the pad 40 made from aluminum from corrosion due to water and is made from a water-resistant material such as fluorinated gel. The protection gel 50 is applied around the pad 40 by using a dispenser or the like and then hardened. Therefore, the protection gel 50 has flowability yet when the protection gel 50 is applied.

If the protection gel 50, which is applied near the pad 40, flows toward the humidity detection section 30 and adheres to the humidity-sensitive film 36, a property of the humidity-sensitive film 36 may be changed so that detection accuracy at ambient humidity may be reduced. For this reason, the dam section 60 is formed on the first surface 20a of the substrate 20 between the humidity detection section 30 and the pad 40. The dam section 60 prevents the protection gel 50, which is applied near the pad 40, from flowing toward the humidity detection section 30 and adhering to the humidity-sensitive film 36.

The dam section 60 includes a dummy wire 61 and a dam humidity-sensitive film 62. The dummy wire 61 is made from the same material as the detection electrodes 31a, 31b and formed on the same plane (the first surface 20a of the substrate 20) as the detection electrodes 31a, 31b. The dam humidity-sensitive film 62 is made from the same material as the humidity-sensitive film 36 and covers at least part of the dummy wire 61. That is, the dam section 60 has a multilayer structure having the dummy wire 61 and the dam humidity-sensitive film 62.

The dam section 60 is described in more detail. The dummy wire 61 is electrically isolated from the electrodes 31a, 31b, 32a, 32b, and the pad 40 of the humidity detection section 30 and does not provide an electrical connection function. As shown in FIG. 3, the dummy wire 61 is formed on the same plane as the detection electrodes 31a, 31b, i.e., on the first surface 20a of the substrate 20. According to the present embodiment, as shown in FIG. 2, the wires 33-35, 45 are formed near an edge of the humidity sensor chip 10 (the first surface 20a of the substrate 20) having the rectangular planar shape. The dummy wire 61 extends in a direction (a direction along one side of the rectangular shape) perpendicular to a facing direction (hereinafter, simply referred to as the "facing direction"), in which the humidity detection section 30 and the pad 40 face each other, to divide the humidity sensor chip 10 having the rectangular planar shape into two regions. Further, multiple dummy wires 61 are arranged side by side in the facing direction. Specifically, the dummy wires 61 are arranged in parallel at regular intervals.

Like the detection electrodes 31a, 31b, the dummy wire 61 is made from aluminum. Therefore, as shown in FIG. 3, the dummy wire 61 is also covered with the protection layer 23, and the dam humidity-sensitive film 62 is formed through the protection layer 23. Like the humidity-sensitive film 36, the dam humidity-sensitive film 62 is made from a polyimide-type material.

Figure 4A:
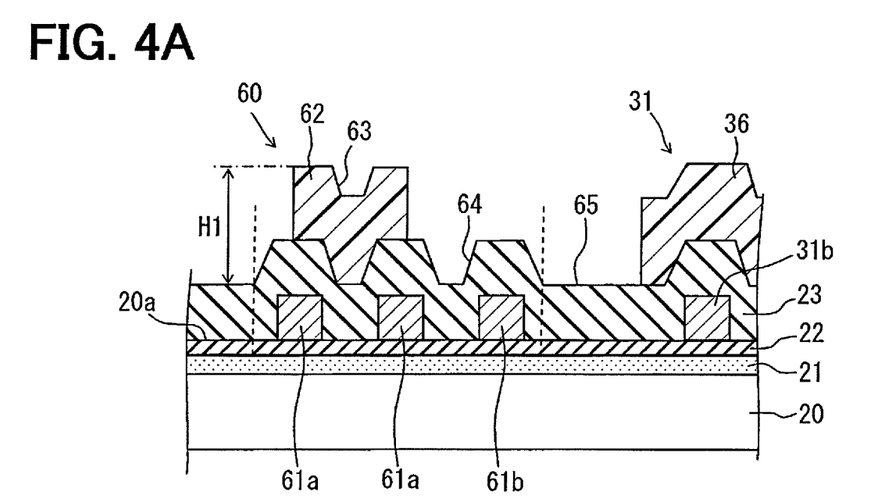
FIG. 4A is a diagram illustrating a cross-sectional view to explain an advantage of a dam section of a structure according to the first embodiment, in which the number of the dummy wires is reduced compared to FIG. 3 for the sake of convenience.

The dam humidity-sensitive film 62 is formed above dummy wires 61a. Specifically, the dam humidity-sensitive film 62 is integrally formed across the dummy wires 61a that are located adjacent to each other in the facing direction. As shown in FIG. 4, since no dummy wire 61a is located between adjacent dummy wires 61a, a recess 63 appears on a surface of the dam humidity-sensitive film 62 between the dummy wires 61a. The dam humidity-sensitive film 62 extends from one to the other of opposing sides of the humidity sensor chip 10 having the rectangular planar shape along an extension direction (a longitudinal direction) of the dummy wire 61a. Thus, the dam humidity-sensitive film 62 divides the humidity sensor chip 10 having the rectangular planar shape into two regions in the facing direction.

Figure 5:
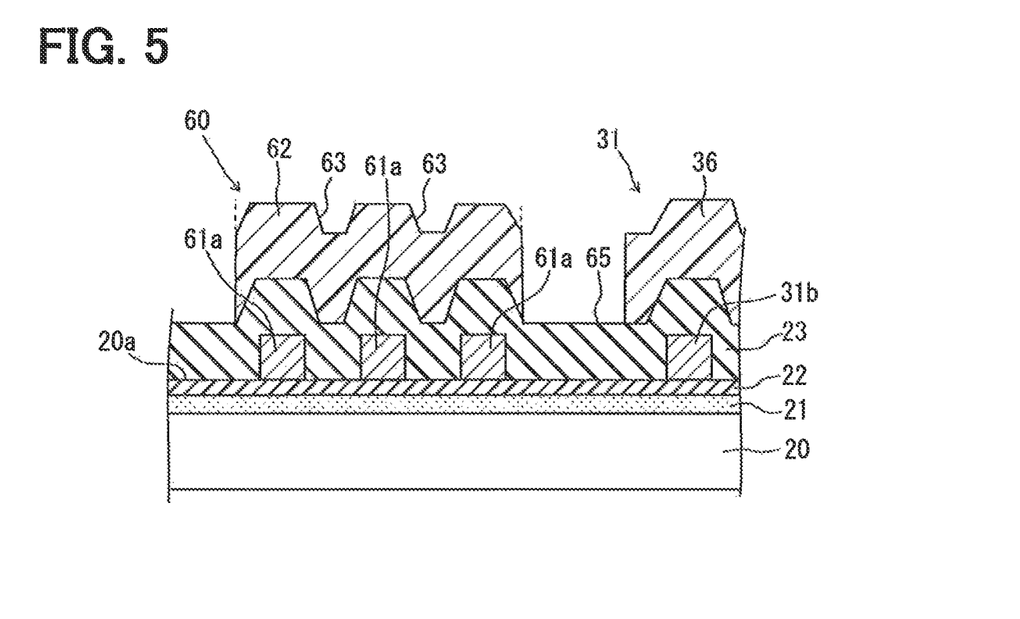
FIG. 5 is a diagram illustrating a cross-sectional view of a dam section according to a modification.

The others of the dummy wires 61 are dummy wires 61b. The dummy wires 61b are exposed outside the dam humidity-sensitive film 62, and only the protection layer 23 is located above the dummy wires 61b. According to the present embodiment, as shown in FIGS. 2-4, the dummy wire 61b is located between the humidity-sensitive film 36 and the dam humidity-sensitive film 62. Since no dummy wire 61 is located between the dummy wire 61b and the dummy wire 61a adjacent to the dummy wire 61b, a recess 64 appears on a surface of the protection layer 23 between the dummy wires 61a, 61b. Although not shown in FIGS. 3 and 4, as shown in FIG. 5, multiple dummy wires 61b are exposed outside the dam humidity-sensitive film 62. Therefore, the recess 64 also appears on the surface of the protection layer 23 between the dummy wires 61b.

The dam section 60 is spaced from the humidity detection section 30 in the facing direction. Specifically, there is a region, where no wire and no electrode are formed, between the dummy wire 61 and the detection electrodes 31a, 31b and the reference electrodes 32a, 32b in the facing direction. Further, the humidity-sensitive film 36 and the dam humidity-sensitive film 62 are completely separated from each other. There is a region, where the humidity-sensitive films 36, 62 are not located, between the humidity-sensitive film 36 and the dam humidity-sensitive film 62 in the facing direction. Accordingly, as shown in FIG. 4, a recess 65 appears on the surface of the protection layer 23 between the humidity detection section 30 and the outermost dummy wire 61 closest to the humidity detection section 30 in the facing direction.

In the humidity sensor chip 10, a capacitance of the capacitor formed in the detection capacitive device 31 changes with a change in ambient relative humidity, and a capacitance of the capacitor formed in the reference capacitive device 32 changes with the change in ambient relative humidity. Further, due to the above structure, the ratio of the change in the capacitance with respect to the change in ambient humidity is different between the detection capacitive device 31 and the reference capacitive device 32. Accordingly, each capacitance is represented by a straight line having a different slope and intercept with respect to ambient relative humidity. In other words, there is a difference in sensitivity between the detection capacitive device 31 and the reference capacitive device 32. Therefore, the ambient relative humidity can be detected based on a difference in the change in capacitance between the detection capacitive device 31 and the reference capacitive device 32.

Further, the humidity-sensitive film 36 formed on the detection electrodes 31a, 31b is made from the same material as the humidity-sensitive film 36 formed on the reference electrodes 32a, 32b. Therefore, an influence of a characteristic of a sensor output (a characteristic of sensitivity on temperature) on temperature due to a characteristic of the humidity-sensitive film 36 on temperature (a characteristic of absorption and desorption of water vapor on temperature) and an influence of aged deterioration of the humidity-sensitive film 36 can be removed.

For example, the humidity sensor chip 10 can be manufactured by a manufacturing method described below.

First, a silicon wafer as the substrate 20 is prepared, and a silicon oxide layer is formed on a surface by thermal oxidation. Then, the diffusion layer 21 is formed by ion implantation of impurities into the surface of the substrate 20 through the silicon oxide layer. Then, the BPSG layer is formed on the silicon oxide layer so that the BPSG layer and the silicon oxide layer can become the insulating layer 22. Then, after the contact hole 22a is formed at a predetermined position of the insulating layer 22, aluminum is deposited all over the first surface 20a of the substrate 20. Then, the electrodes 31a, 31b, 32a, 32b, the wires 33-35 including the pad 40 (41-44), and the dummy wire 61 are formed by patterning. In this way, the electrodes 31a, 31b, 32a, and 32b of the humidity detection section 30 and the dummy wire 61 (dam wire) are formed in the same process by using the same material.

Then, a silicon nitride layer as the protection layer 23 is formed all over the first surface 20a of the substrate 20, and the pad 40(41-44) is exposed by patterning. Then, after precursor is coated on the first surface 20a of the substrate 20, for example, by a spin coating method, a hardening treatment is performed. Then, the humidity-sensitive film 36 and the dam humidity-sensitive film 62 are formed by patterning. In this way, the humidity-sensitive film 36 of the humidity detection section 30 and the dam humidity-sensitive film 62 are formed in the same process by using the same material.

Then, the substrate 20 is diced into chips. Then, after the bonding wire 115 is connected to the corresponding pad 40(41-44), the protection gel 50 is applied around the pad 40 by using a dispenser or the like. Then, the protection gel 50 is hardened. Thus, the humidity sensor chip 10 can be manufactured.

Advantages of the humidity sensor chip 10 and the manufacturing method according to the present embodiment are described below.

According to the present embodiment, the dummy wire 61 as a dam wire of the dam section 60 and the detection electrodes 31a, 31b of the humidity detection section 30 are formed in the same process by using the same material. Further, the dummy wire 61 is formed on the same plane (on the first surface 20a of the substrate 20) as the detection electrodes 31a, 31b. Further, the dam humidity-sensitive film 62 of the dam section 60 and the humidity-sensitive film 36 of the humidity detection section 30 are formed in the same process by using the same material. Since the dam section 60 is manufactured by using the same material as the humidity detection section 30, a structure of the humidity sensor chip 10 can be simplified. Further, since the dam section 60 is formed by using the manufacturing process in which the humidity detection section 30 is formed, the manufacturing process can be simplified.

Figure 4B:
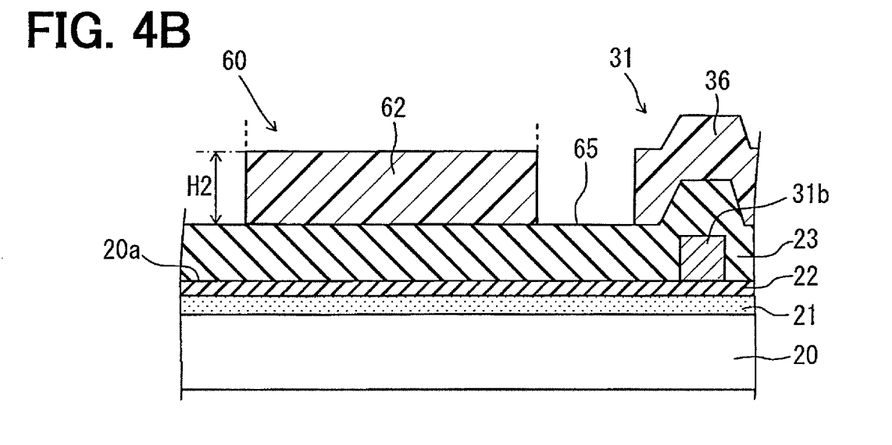
FIG. 4B is a diagram illustrating a cross-sectional view of a conventional structure as a comparison example.

Further, as shown in FIG. 4B, when the dam section 60 has only the dam humidity-sensitive film 62 without the dummy wire 61 as the dam wire, a height H2 of the dam section 60 at a position where no dummy wire 61 is on the insulating layer 22 (at a position where the protection layer 23 is in contact with the insulating layer 22) is equal to a thickness of the dam humidity-sensitive film 62. As described above, since the humidity-sensitive film 36 and the dam humidity-sensitive film 62 are formed in the same process by using the same material, it is difficult that the dam humidity-sensitive film 62 is made extremely thicker than the humidity-sensitive film 36. Therefore, using the dam humidity-sensitive film 62 only does not allow the dam section 60 to have enough height.

In contrast, according to the present embodiment, as shown in FIG. 4A, the dam section 60 has a multilayer structure in which the dam humidity-sensitive film 62 is stacked on the dummy wire 61a through the protection layer 23. Accordingly, a height H1 of the dam section 60 at a position where no dummy wire 61 is on the insulating layer 22 (at a position where the protection layer 23 is in contact with the insulating layer 22) is equal to the sum of a thickness of the dam humidity-sensitive film 62 and a thickness of the dummy wire 61 (61a). Therefore, the height of the dam section 60 can be increased as compared to when the dam section 60 has only the dam humidity-sensitive film 62. Thus, since the protection gel 50 is less likely to flow over the dam section 60, adhesion of the protection gel 50 to a surface of the humidity-sensitive film 36 can be effectively reduced. In FIGS. 4A and 4B, a region between broken lines indicates a formation region of the dam section 60.

As described above, according to the present embodiment, the structure and the manufacturing process of the humidity sensor chip 10 can be simplified, and the adhesion of the protection gel 50 to the humidity-sensitive film 36 can be effectively reduced.

Further, according to the present embodiment, the dummy wire 61 as the dam wire is electrically isolated from the detection electrodes 31a, 31b, and the pad 40 and does not provide an electrical connection function. In such an approach, the height of the dam section 60 can be increased without a wire 81 of a circuit section 80 which is described later. Further, since the dummy wire 61 does not provide an electrical connection function, signal quality can be maintained even when multiple dummy wires 61 are arranged side by side and covered with the dam humidity-sensitive film 62.

By the way, viscous drag depends on a shape of an object in contact with a viscous member such as the protection gel 50. Specifically, compared to a plane, since a structure with a projection and a recess has a large contact area with the viscous member, the viscous drag is large. That is, the protection gel 50 cannot easily flow.

Regarding this matter, according to the present embodiment, multiple dummy wires 61 are arranged side by side in the facing direction, in which the humidity detection section 30 and the pad 40 face each other, and the dam section 60 has the recesses 63, 64 between adjacent dummy wires 61. Specifically, the dam humidity-sensitive film 62 is integrally formed across the dummy wires 61a that are located adjacent to each other, and the recess 63 is located on the surface of the dam humidity-sensitive film 62 between the dummy wires 61a. The dummy wire 61 includes the dummy wire 61b exposed outside the dam humidity-sensitive film 62, and the recess 64 is located between the dummy wire 61b and the dummy wire 61 (61a or 61b) adjacent to this dummy wire 61b.

When the dam section 60 has the recesses 63, 64 between the dummy wires 61 (at a position where no dummy wire 61 exists), the contact area between the dam section 60 and the protection gel 50 until the protection gel 50 flows over the dam section 60 is increased without increasing the size of the dam section 60 in the facing direction. In other words, a length of a flow path necessary for the protection gel 50 to flow over the dam section 60 is increased. Thus, the viscous drag of the flowing protection gel 50 is increased. Further, part of the protection gal 50 can be stored in the recesses 63, 64. Therefore, the adhesion of the protection gel 50 to the humidity-sensitive film 36 can be more effectively reduced.

In particular, according to the present embodiment, the dummy wire 61b exposed outside the dam humidity-sensitive film 62 is located between the dam humidity-sensitive film 62 and the humidity-sensitive film 36 in the facing direction in which the humidity detection section 30 and the pad 40 face each other. In other words, the recess 64 is located between the dam humidity-sensitive film 62 and the humidity-sensitive film 36. Therefore, the dam humidity-sensitive film 62 and the humidity-sensitive film 36 can be spaced away from each other while increasing the contact area between the dam section 60 and the protection gel 50.

Generally, the depth of the recesses 63, 64 formed by multiple dummy wires 61 (dam wires) becomes larger, as the distance from the dummy wire 61 in the height direction is smaller. Regarding this, according to the present embodiment, while the recess 63 is formed on the dam humidity-sensitive film 62, the recess 64 is formed on the surface of the protection layer 23 by the dummy wire 61b which is exposed outside the dam humidity-sensitive film 62. Since the recess 64 is located closer to the dummy wire 61 than the recess 63 in the height direction, the depth of the recess 64 is larger than the depth of the recess 63. Therefore, the adhesion of the protection gel 50 to the humidity-sensitive film 36 can be more effectively reduced.

Further, according to the present embodiment, as shown in FIG. 2, the dam humidity-sensitive film 62 and the humidity-sensitive film 36 are separated from each other. Therefore, even when the protection gel 50 reaches a surface (a top surface) of the dam humidity-sensitive film 62, the protection gel 50 does not reach the surface of the humidity-sensitive film 36 by flowing continuously over a member made from the same material (polyimide). Further, the length of the flow path to the humidity-sensitive film 36 is increased. Therefore, the adhesion of the protection gel 50 to the humidity-sensitive film 36 can be more effectively reduced. In particular, according to the present embodiment, the dam section 60 divides the humidity sensor chip 10 (the first surface 20a of the substrate 20) having the rectangular planar shape into two regions in the facing direction. Therefore, the dam section 60 effectively restrains the protection gel 50 from flowing to the humidity detection section 30.

Further, according to the present embodiment, the recess 65 is located between the humidity detection section 30 and the outermost dummy wire 61b closest to the humidity detection section 30 in the facing direction. The contact area between the dam section 60 and the protection gel 50 is increased by the recess 65. Further, the protection gel 50 can be stored in the recess 65.

(Modification)

In the above embodiment, as shown in FIGS. 3 and 4, the dam section 60 has the dummy wire 61a covered with the dam humidity-sensitive film 62, the dummy wire exposed outside the dam humidity-sensitive film 62, and the recesses 63, 64. Alternatively, for example, as shown in FIG. 5, the dam section 60 can have only the dummy wire 61a covered with the dam humidity-sensitive film 62 so that only the recess 63 on the surface of the dam humidity-sensitive film 62 can be formed. Even in such a structure, since the height of the dam section 60 becomes large, the adhesion of the protection gel 50 to the surface of the humidity-sensitive film 36 can be more effectively reduced. In addition, since the dam humidity-sensitive film 62 has the recess 63, the adhesion of the protection gel 50 to the humidity-sensitive film 36 can be more effectively reduced.

In FIG. 5, in the facing direction in which the pad 40 and the humidity detection section 30 face each other, an end of the dam humidity-sensitive film 62 on the pad 40 side is located closer to the pad 40 than an end of the dummy wire 61a on the pad 40 side, and an end of the dam humidity-sensitive film 62 on the humidity detection section 30 side is located closer to the humidity detection section 30 than an end of the dummy wire 61a on the humidity detection section 30 side. Alternatively, the end of the dam humidity-sensitive film 62 on the pad 40 side can be located above the end of the dummy wire 61a on the pad 40 side. Likewise, the end of the dam humidity-sensitive film 62 on the humidity detection section 30 side can be located above the end of the dummy wire 61a on the humidity detection section 30 side.

Figure 6:
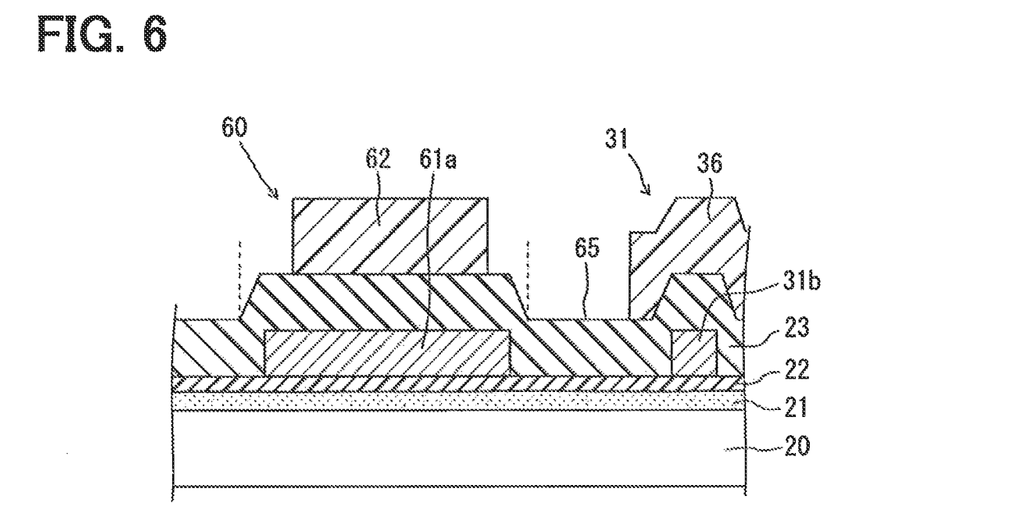
FIG. 6 is a diagram illustrating a cross-sectional view of a dam section according to a modification.

For example, as shown in FIG. 6, the dam section 60 can have only one dummy wire 61a as the dummy wire 61. Since the height of the dam section 60 becomes large, the adhesion of the protection gel 50 to the surface of the humidity-sensitive film 36 can be more effectively reduced. In FIG. 6, in the facing direction in which the pad 40 and the humidity detection section 30 face each other, both the end of the dam humidity-sensitive film 62 on the pad 40 side and the end of the dam humidity-sensitive film 62 on the humidity detection section 30 side are located above the dummy wire 61a. Alternatively, the end of the dam humidity-sensitive film 62 on the pad 40 side can be located closer to the pad 40 than the end of the dummy wire 61a on the pad 40 side, and the end of the dam humidity-sensitive film 62 on the humidity detection section 30 side can be located closer to the humidity detection section 30 than the end of the dummy wire 61a on the humidity detection section 30 side.

Figure 7:
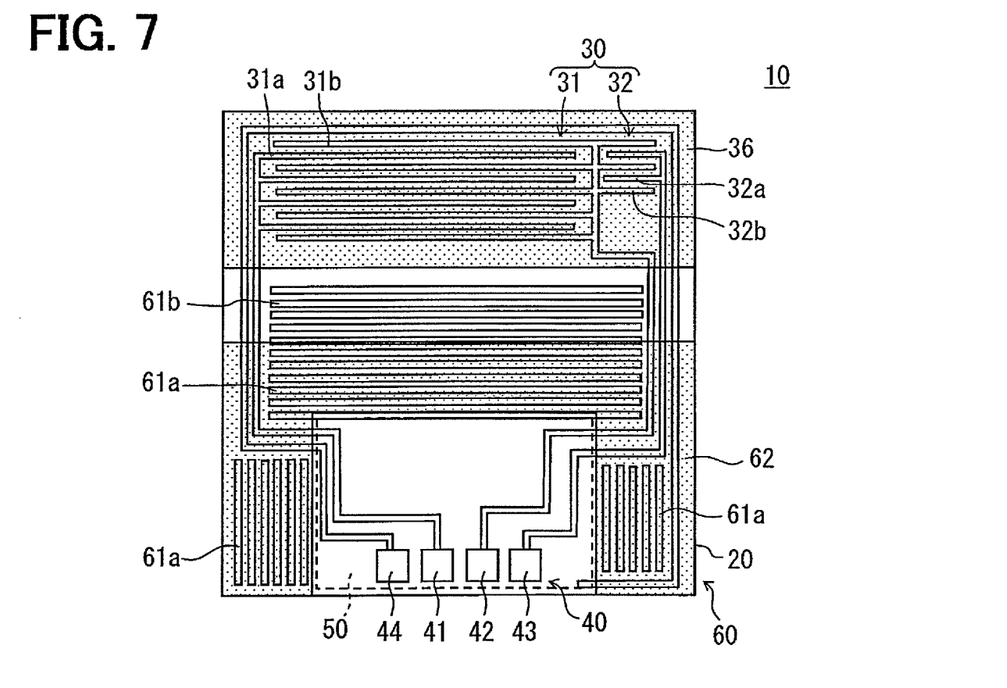
FIG. 7 is a diagram illustrating a plan view of a layout of a dam section on a substrate according to a modification, in which a detection electrode, a reference electrode, a wire for connecting the electrodes to a pad, and a dummy wire are indicated by a solid line, and the protection gel is indicated by a broken line for the sake of convenience.

In the above embodiment, the dam section 60 extends in the direction perpendicular to the facing direction, in which the humidity detection section 30 and the pad 40 face each other, to divide the humidity sensor chip 10 (the first surface 20a of the substrate 20) having the rectangular planar shape into two regions. However, a layout of the dam section 60 is not limited to the above example. For example, as shown in FIG. 7, the dam section 60 can have a rectangular C-shape in plan view. The dam section 60 can be located between the pad 40 and the humidity detection section 30 in the facing direction and located on both sides of the pad 40 in a direction perpendicular to the facing direction. As shown in FIG. 7, since the pad 40 is located along an edge of one side of the substrate 20 having the rectangular planar shape, the dam section 60 surrounds the pad 40 on the first surface 20a of the substrate 20. Thus, since the protection gel 50 is likely to flow in a direction away from the humidity detection section 30, the adhesion of the protection gel 50 to the humidity-sensitive film 36 can be more effectively reduced.

Figure 8:
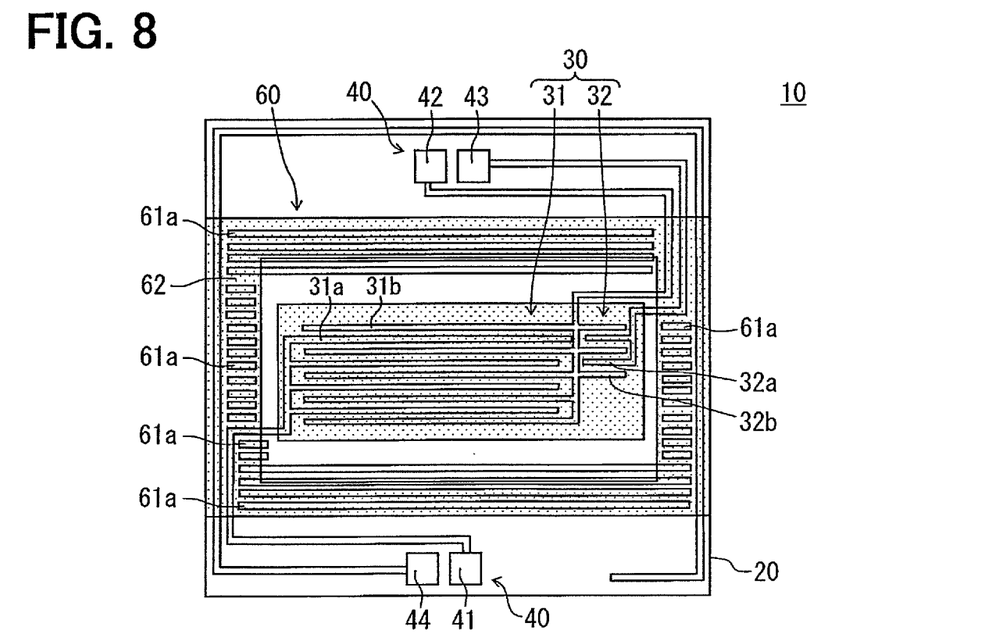
FIG. 8 is a diagram illustrating a plan view of a layout of a dam section on a substrate according to a modification, in which a detection electrode, a reference electrode, a wire for connecting the electrodes to a pad, and a dummy wire are indicated by a solid line, and a protection gel is indicated by a broken line for the sake of convenience.

Further, as shown in FIG. 8, the dam section 60 can surround the humidity detection section 30. In FIG. 8, the dam section 60 has a rectangular ring shape, and the humidity detection section 30 is located inside the dam section 60. In FIG. 8, the pad 40 is located on each side across the humidity detection section 30 and the dam section 60. Even in such a structure, the adhesion of the protection gel 50 to the humidity-sensitive film 36 can be more effectively reduced. In FIGS. 7 and 8, the dummy wire 61 is formed in portions, where the wires 33-35 and 45 are not formed, within the formation region of the dam section 60.

In the above embodiment, the detection electrodes 31a, 31b, the reference electrodes 32a, 32b, and the dummy wire 61 are covered with the protection layer 23. However, when the detection electrodes 31a, 31b, the reference electrodes 32a, 32b, and the dummy wire 61 are made from a material having corrosion resistance to water, the protection layer 23 can be omitted. In this case, the dam humidity-sensitive film 62 is in contact with the dummy wire 61a, and the recess 64 is located adjacent to the dummy wire 61b.

In the above embodiment, the wires 33-35 and 45, which are connected to the pad 40, are made from the same aluminum martial as the pad 40, and formed on the same plane (the first surface 20a of the substrate 20) as the detection electrodes 31a, 31b. Alternatively, at least part of the wire passing through the formation region of the dam section 60 can be provided by a diffusion layer. In such an approach, the dummy wire 61 can be formed so that the dummy wire 61 can extend between two opposing sides of the humidity sensor chip 10 (the first surface 20a of the substrate 20) having the rectangular planar shape. Accordingly, the height of the dam section 60 can be increased throughout a region between the two opposing sides.

In the above embodiment, the humidity sensor chip 10 has the diffusion layer 21, the pad 44, and the wire 45, which are electrically connected to the diffusion layer 21. However, it is not always necessary that the humidity sensor chip 10 has these.

Second Embodiment

In the first embodiment, the humidity-sensitive film 36 and the dam humidity-sensitive film 62 are separated from each other. In contrast, according to the present embodiment, as shown in FIG. 9, the humidity-sensitive film 36 and the dam humidity-sensitive film 62 are integrated together through a connection humidity-sensitive film 70 which is made from the same material (polyimide) as the humidity-sensitive film 36.

Figure 9:
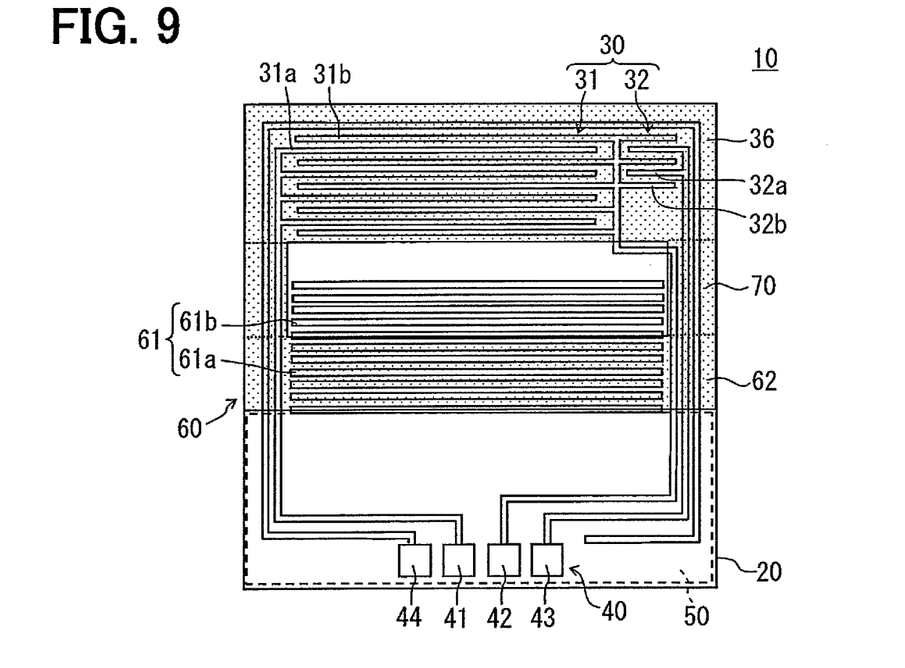
FIG. 9 is a diagram illustrating a plan view of a humidity sensor according to a second embodiment, in which a detection electrode, a reference electrode, a wire for connecting the electrodes to a pad, and a dummy wire are indicated by a solid line, and a protection gel is indicated by a broken line for the sake of convenience.

In an example shown in FIG. 9, like in the first embodiment (refer to FIG. 2), the dam humidity-sensitive film 62 extends between two opposing sides of the first surface 20a of the substrate 20 having the rectangular planar shape to divide the first surface 20a into two regions. Further, the width of the dam humidity-sensitive film 62 is smaller than the width of the humidity-sensitive film 36 in a direction perpendicular to a longitudinal direction of the dam humidity-sensitive film 62 (in the facing direction in which the humidity detection section 30 and the pad 40 face each other). The connection humidity-sensitive film 70 is connected to each end of the dam humidity-sensitive film 62 in the longitudinal direction of the dam humidity-sensitive film 62.

The humidity sensor chip 10 having the above structure can provide the following advantages in addition to the advantages described in the first embodiment. It is noted that the dam section 60 except the connection humidity-sensitive film 70 can provide the same advantages as the recess (64, 65).

According to the present embodiment, the connection humidity-sensitive film 70 integrates the humidity-sensitive film 36 and the dam humidity-sensitive film 62 into a single humidity-sensitive film. Thus, the total contact area between the humidity-sensitive film and the substrate 20 is increased, so that detachments of the humidity-sensitive film 36 and the dam humidity-sensitive film 62 during a dicing process can be reduced. In particular, detachment of the dam humidity-sensitive film 62, which is narrower than the humidity-sensitive film 36, can be reduced.

The dam humidity-sensitive film 62 is connected to the humidity-sensitive film 36 through the connection humidity-sensitive film 70 at both ends in the longitudinal direction and separated from the humidity-sensitive film 36 in the middle in the longitudinal direction. The pad 40 is located in the middle in the longitudinal direction. That is, even when the protection gel 50 reaches a surface of a middle portion of the dam humidity-sensitive film 62, which is located close to the pad 40 in the facing direction in which the humidity detection section 30 and the pad 40 face each other, the protection gel 50 does not reach the surface of the humidity-sensitive film 36 by flowing continuously over a member made from the same material (polyimide). Further, the length of the flow path to the humidity-sensitive film 36 is increased. Therefore, the adhesion of the protection gel 50 to the humidity-sensitive film 36 can be more effectively reduced.

Third Embodiment

Figure 10:
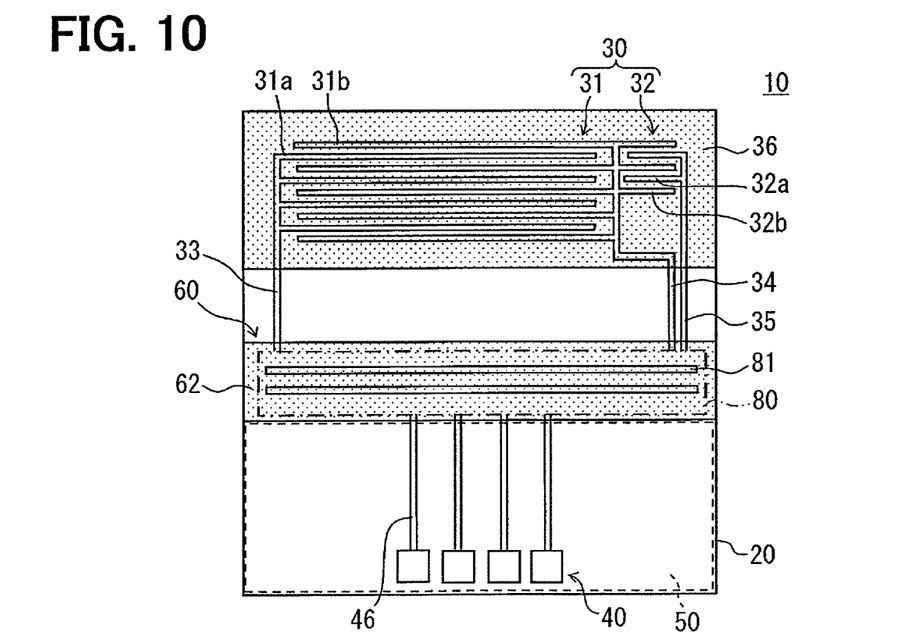
FIG. 10 is a diagram illustrating a plan view of a humidity sensor according to a third embodiment, in which a detection electrode, a reference electrode, a wire for connecting the electrodes to a circuit section, a wire of the circuit section included in a dam section, a wire for connecting the circuit section to a pad are indicated by a solid line, a protection gel is indicated by a broken line, and portions of the circuit section except the wire included in the dam section is indicated by a chain line.

In the above embodiment, the humidity sensor chip 10 is a separate chip from the circuit chip 113, and the dummy wire 61, which is electrically disconnected from the electrodes 31a, 31b, 32a, 32b and the pad 40 of the humidity detection section 30, is used as the dam wire. In contrast, according to the present embodiment, as shown in FIG. 10, a circuit section 80 of the circuit chip 113 is integrated into the humidity sensor chip 10, and a wire 81 of the circuit section 80 is used as the dam wire. The circuit section 80 includes a circuit (e.g., a C-V conversion circuit) for processing an output of the humidity detection section 30.

In an example shown in FIG. 10, the circuit section 80 is formed between the humidity detection section 30 and the pad 40 in the facing direction in which the humidity detection section 30 and the pad 40 face each other. The wire 81 of the circuit section 80 is made from the same material (aluminum) as the detection electrodes 31a, 31b. Like the dummy wire 61, the wire 81 extends in a direction perpendicular to the facing direction. Further, multiple wires 81 are arranged side by side in the facing direction. In FIG. 2, two wires 81 are covered with the dam humidity-sensitive film 62. However, the number of the wires 81 is not limited to the above example. Like the dummy wire 61, the wire 81 can includes not only a wire covered with the dam humidity-sensitive film 62 but also a wire exposed outside the dam humidity-sensitive film 62.

It is noted that the wires 33-35 are electrically connected to the electrodes 31a, 31b, 32a, 32b of the humidity detection section 30 and the circuit section 80. The wire 46 is connected to the pad 40 and the circuit section 80.

The humidity sensor chip 10 having the above structure can provide the following advantages in addition to the advantages described in the first embodiment. According to the present embodiment, the circuit section 80 is integrated in the humidity sensor chip 10. Therefore, the size of the humidity detection apparatus 100 can be reduced. Further; the wire 81 of the circuit section 80 formed in the same substrate 20 as the humidity detection section 30 is used as the dam wire. Therefore, the size of the humidity sensor chip 10 can be small as compared to when the dummy wire 61 is used.

According to the present embodiment, the humidity sensor chip 10 and the circuit chip 113 are integrated in one chip. Therefore, one of the islands 111, 112 of the humidity detection apparatus 100 shown in FIG. 1 can be eliminated, and the pad 40 of the humidity sensor chip 10 is connected to the lead 114 through the bonding wire 115.

While the present disclosure has been described with reference to embodiments thereof, it is to be understood that the disclosure is not limited to the embodiments. The present disclosure is intended to cover various modifications and equivalent arrangements within the spirit and scope of the present disclosure.

According to the embodiments, the humidity detection section 30 includes the detection capacitive device 31 and the reference capacitive device 32. Alternatively, the humidity detection section 30 can include only the detection capacitive device 31.

According to the embodiments, the humidity sensor chip 10 is configured as a capacitive humidity sensor for detecting a change in ambient humidity based on a change in capacitance between the detection electrodes 31a, 31b. However, the detection principle is not limited to this. For example, the humidity sensor chip 10 can be configured as a resistive humidity sensor for detecting a change in ambient humidity based on a change in impedance of the humidity-sensitive film 36.

What is claimed is:

1. A humidity sensor comprising:
   a humidity detention section including a pair of detection electrodes and a humidity-sensitive film, the detection electrodes facing each other on a humidity detection section formation surface of a substrate, the humidity-sensitive film covering the detection electrodes and a gap between the detection electrodes;
   a pad section as an external connection terminal, the pad section being spaced from the humidity detection section on the humidity detection section formation surface of the substrate and covered with a protection gel section under a condition where a bonding wire is connected to the pad section; and
   a dam section located between the humidity detection section and the pad section on the humidity detection section formation surface of the substrate to restrain the protection gel section from flowing from the pad section side to the humidity detection section side, wherein
   the dam section includes a dam wire and a dam humidity-sensitive film,
   the dam wire is made from the same material as the detection electrodes and located on the same surface as the detection electrodes,
   the dam humidity-sensitive film is made from the same material as the humidity-sensitive film and covers at least part of the dam wire,
   a first recess is formed on the dam section to receive a portion of the protection gel section in a case where the protection gel section flows to the dam section; and
   a second recess is formed at a location between the dam section and the humidity detection section to receive another portion of the protection gel section in a case where the protection gel section flows to the second recess formed at the location between the dam section and the humidity detection section.

2. The humidity sensor according to claim 1, further comprising:
   a plurality of dam wires including the dam wire and arranged side by side in a facing direction in which the humidity detection section and the pad section face each other, wherein
   the first recess formed in the dam section is between adjacent dam wires.

3. The humidity sensor according to claim 2, wherein
   the dam humidity-sensitive film covers at least two adjacent dam wires and a gap between the at least two adjacent dam wires, and
   the first recess is located between the at least two adjacent dam wires.

4. The humidity sensor according to claim 2, wherein
   at least one of the plurality of dam wires is exposed outside the dam humidity-sensitive film, and
   the first recess is located between the exposed dam wire and the dam wire adjacent to the exposed dam wire.

5. The humidity sensor according to claim 4, wherein
   the exposed dam wire is located between the dam humidity-sensitive film and the humidity-sensitive film in the facing direction in which the humidity detection section and the pad section face each other.

6. The humidity sensor according to claim 1, wherein
   the detection electrodes, the pad section, and the dam wire are made from the same material,
   surfaces of the detection electrodes and a surface of the dam wire are collectively covered with the protection layer, and
   the humidity-sensitive film and the dam humidity-sensitive film are formed on the protection layer.

7. The humidity sensor according to claim 1, wherein
   the dam wire includes a dummy wire having no electrical connection function and electrically isolated from the detection electrodes and the pad section.

8. The humidity sensor according to claim 1, further comprising:
   a circuit section formed in the substrate and capable of processing an output signal of the humidity detection section, wherein
   the dam wire includes a wire of the circuit section.

9. The humidity sensor according to claim 1, wherein
   the humidity-sensitive film and the dam humidity-sensitive film are separated from each other.

10. The humidity sensor according to claim 9, wherein
    the humidity detection section formation surface of the substrate has a rectangular shape, and
    the dam humidity-sensitive film of the dam section extends from one side to another side opposite to the one side of the humidity detection section formation surface to divide the humidity detection section formation surface into two regions.

11. The humidity sensor according to claim 9, wherein
    the dam section surrounds the humidity detection section.

12. The humidity sensor according to claim 1, wherein
    the humidity-sensitive film and the dam humidity-sensitive film are integrated together through a connection humidity-sensitive film which is made from the same material as the humidity-sensitive film.

13. The humidity sensor according to claim 12, wherein
    the humidity detection section formation surface of the substrate has a rectangular shape,
    the dam humidity-sensitive film of the dam section extends from one side to another side opposite to the one side of the humidity detection section formation surface to divide the humidity detection section formation surface into two regions,
    a width of the dam humidity-sensitive film is smaller than a width of the humidity-sensitive film in a direction perpendicular to a longitudinal direction of the dam humidity-sensitive film, and
    the connection humidity-sensitive film is connected to a portion of the dam humidity-sensitive film.

14. The humidity sensor according to claim 12, wherein
the dam section has a rectangular C-shape in plan view and is located between the pad section and the humidity detection section, and
the dam section is located on both sides of the pad section in a direction perpendicular to the facing direction in which the humidity detection section and the pad section face each other.

15. The humidity sensor according to claim 1, wherein
the humidity detection section detects a change in ambient humidity based on a change in capacitance between the detection electrodes.

16. A method of manufacturing a humidity sensor comprising:
an electrode formation step of forming a pair of detection electrodes on a predetermined surface of a substrate;
a humidity detection section formation step of forming a humidity detection section by forming a humidity-sensitive film to cover the detection electrodes and a gap between the detection electrodes; and
a pad section formation step of forming a pad section as an external connection terminal in such a manner that the pad section is spaced from the humidity detection section on the surface of the substrate and covered with a protection gel section under a condition where a bonding wire is connected to the pad section, wherein
the electrode formation step includes a dam wire formation step of forming a dam wire on the surface of the substrate between the humidity detection section and the pad section by using the same material as the detection electrodes, and the humidity detection section formation step includes a dam section formation step of forming a dam section, which restrains the protection gel section from flowing from the pad section side to the humidity detection section side, by forming a dam humidity-sensitive film to cover at least part of the dam wire by using the same material as the humidity-sensitive film,
a first recess is formed on the dam section to receive a portion of the protection gel section in a case where the protection gel section flows to the dam section; and
a second recess is formed at a location between the dam section and the humidity detection section to receive another portion of the protection gel section in a case where the protection gel section flows to the second recess formed at the location between the dam section and the humidity detection section.

* * * * *